United States Patent
Kurz et al.

(10) Patent No.: US 6,306,153 B1
(45) Date of Patent: *Oct. 23, 2001

(54) VASOOCCLUSIVE COIL

(75) Inventors: Daniel R. Kurz, Sunnyvale; David A. Ferrera, San Francisco; Peter Wilson, Foster City, all of CA (US)

(73) Assignee: Micrus Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/557,127

(22) Filed: Apr. 25, 2000

Related U.S. Application Data

(63) Continuation of application No. 09/139,258, filed on Aug. 25, 1998, now Pat. No. 6,136,015.

(51) Int. Cl.$^7$ .................................................. A61M 29/00
(52) U.S. Cl. ............................................................. 606/191
(58) Field of Search .................................. 606/191, 108, 606/200, 198

(56) References Cited

U.S. PATENT DOCUMENTS

| | | |
|---|---|---|
| 1,341,052 | 5/1920 | Gale . |
| 1,667,730 | 5/1928 | Green . |
| 2,078,182 | 4/1937 | MacFarland . |
| 2,549,335 | 4/1951 | Rahthus . |
| 3,334,629 | 8/1967 | Cohn . |
| 3,452,742 | 7/1969 | Muller . |
| 3,649,224 | 3/1972 | Anderson et al. . |
| 3,868,956 | 3/1975 | Alfidi et al. . |
| 4,041,931 * | 8/1977 | Elliot et al. ....................... 606/108 X |
| 4,494,531 | 1/1985 | Gianturco . |
| 4,512,338 | 4/1985 | Balko et al. . |
| 4,638,803 | 1/1987 | Rand . |
| 4,650,472 | 3/1987 | Bates . |
| 4,655,771 | 4/1987 | Wallsten . |
| 4,718,907 | 1/1988 | Karowski et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,820,289 | 4/1989 | Cury et al. . |
| 4,820,298 | 4/1989 | Leveen et al. . |

(List continued on next page.)

OTHER PUBLICATIONS

Retrievable Gianturco–Coil Introducer, By Jeffrey Hawkins, Ronald G. Quisling, MD, J. Parker Mickle, MD an Irvin F. Hawkins, MD (Radiology 1986) From the Depts. of Radiology and Neurosurgery, Uniersity of Florida Medical Center and Hawk Prototype Equipment, gainesville, FL .

*Primary Examiner*—Olik Chaudhuri
*Assistant Examiner*—Hoa B. Trinh
(74) *Attorney, Agent, or Firm*—Fulwider Patton Lee & Uttecht, LLP

(57) ABSTRACT

The vasoocclusive coil has a primary coil configuration with a helical loop at at least one end. The terminal helical loop can have a J-shaped configuration, preferably with a loop diameter of about 2 mm. The coil is preferably provided with helical loops at both ends, with helical loop at the proximal and distal ends of the coil acting as an anchor to prevent the coil from coming free from the location being treated and escaping into the vasculature. In a presently preferred embodiment both ends of the coil have a J-shape. In another presently preferred aspect, the vasoocclusive coil includes one or more loops intermediate the ends of the coil. The device is formed from a multi-stranded micro-cable having a plurality of flexible strands of a shape memory material and at least one radiopaque strand. The strands can be made of a shape memory nickel titanium alloy, that is highly flexible at a temperature appropriate for introduction into the body via a catheter, and that after placement will take on the therapeutic shape.

23 Claims, 8 Drawing Sheets

U.S. PATENT DOCUMENTS

| | | |
|---|---|---|
| 4,830,003 | 5/1989 | Wolff et al. . |
| 4,838,803 | 6/1989 | Kondo . |
| 4,850,960 | 7/1989 | Grayzel . |
| 4,856,516 | 8/1989 | Hillstead . |
| 4,954,126 | 9/1990 | Wallsten . |
| 4,957,479 | 9/1990 | Roemer . |
| 4,957,501 | 9/1990 | Lahille et al. . |
| 4,990,155 | 2/1991 | Wilkoff . |
| 4,994,069 | 2/1991 | Ritchart et al. . |
| 5,025,799 | 6/1991 | Wilson . |
| 5,026,377 | 6/1991 | Burton et al. . |
| 5,041,084 | 8/1991 | DeVries et al . |
| 5,064,435 | 11/1991 | Porter . |
| 5,071,407 | 12/1991 | Termin et al. . |
| 5,104,404 | 4/1992 | Wolff . |
| 5,108,407 | 4/1992 | Geremia et al. . |
| 5,122,136 | 6/1992 | Guglielmi et al. . |
| 5,133,731 | 7/1992 | Butler et al. . |
| 5,133,732 | 7/1992 | Wiktor . |
| 5,135,494 | 8/1992 | Engelson et al. . |
| 5,139,243 | 8/1992 | Balsells . |
| 5,141,502 | 8/1992 | MaCaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,176,625 | 1/1993 | Brisson . |
| 5,176,661 | 1/1993 | Evard et al. . |
| 5,183,085 | 2/1993 | Timmermans . |
| 5,186,992 | 2/1993 | Kite, III . |
| 5,203,772 | 4/1993 | Hammerslag et al. . |
| 5,217,484 | 6/1993 | Marks . |
| 5,222,969 | 6/1993 | Gillis . |
| 5,226,911 | 7/1993 | Chee et al. . |
| 5,228,453 | 7/1993 | Sepetka . |
| 5,234,456 | 8/1993 | Silvestrini . |
| 5,238,004 | 8/1993 | Sahatjian et al. . |
| 5,242,462 | 9/1993 | El-Nounou et al. . |
| 5,250,071 | 10/1993 | Palermo . |
| 5,256,146 | 10/1993 | Ensminger et al. . |
| 5,304,142 | 4/1994 | Liebl et al. . |
| 5,304,194 | 4/1994 | Chee et al. . |
| 5,312,415 | 5/1994 | Palermo . |
| 5,334,210 | 8/1994 | Gianturo . |
| 5,336,205 | 8/1994 | Zenzen et al. . |
| 5,342,387 | 8/1994 | Summers . |
| 5,350,397 | 9/1994 | Palermo et al. . |
| 5,354,295 | 10/1994 | Guglielmi et al. . |
| 5,379,779 | 1/1995 | Rowland et al. . |
| 5,382,259 | 1/1995 | Phelps et al. . |
| 5,441,516 | 8/1995 | Wang et al. . |
| 5,443,478 | 8/1995 | Purdy . |
| 5,514,176 | 5/1996 | Bosley, Jr. . |
| 5,522,836 | 6/1996 | Palermo . |
| 5,527,338 | 6/1996 | Purdy . |
| 5,540,680 | 7/1996 | Guglielmi et al. . |
| 5,540,701 | 7/1996 | Sharkey et al. . |
| 5,549,624 | 8/1996 | Mirigian et al. . |
| 5,562,641 | 10/1996 | Flomenblit et al. . |
| 5,569,245 | 10/1996 | Guglielmi et al. . |
| 5,582,619 | 12/1996 | Ken . |
| 5,601,600 | 2/1997 | Ton . |
| 5,607,445 | 3/1997 | Summers . |
| 5,624,461 | 4/1997 | Mariant . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,558 * | 7/1997 | Horton ................................. 606/191 |
| 5,649,949 | 7/1997 | Wallace et al. . |
| 5,667,522 | 9/1997 | Floimenblit et al. . |
| 5,669,931 | 9/1997 | Kupiecki et al. . |
| 5,676,697 | 10/1997 | McDonald . |
| 5,690,643 | 11/1997 | Wijay . |
| 5,690,666 | 11/1997 | Berenstein et al. . |
| 5,690,667 | 11/1997 | Gia . |
| 5,690,671 | 11/1997 | McGurk et al. . |
| 5,693,067 | 12/1997 | Purdy . |
| 5,718,711 | 2/1998 | Berenstein et al. . |
| 5,725,534 | 3/1998 | Rasmussen . |
| 5,725,567 | 3/1998 | Wolff et al. . |
| 5,733,329 | 3/1998 | Wallace et al. . |
| 5,743,905 | 4/1998 | Eder et al. . |
| 5,746,769 | 5/1998 | Ton et al. . |
| 5,749,891 | 5/1998 | Ken et al. . |
| 5,766,160 | 6/1998 | Samson et al. . |
| 5,800,453 | 9/1998 | Gia . |
| 5,800,455 | 9/1998 | Palermo et al. . |
| 5,868,754 * | 2/1999 | Levine et al. ........................ 606/108 |

\* cited by examiner

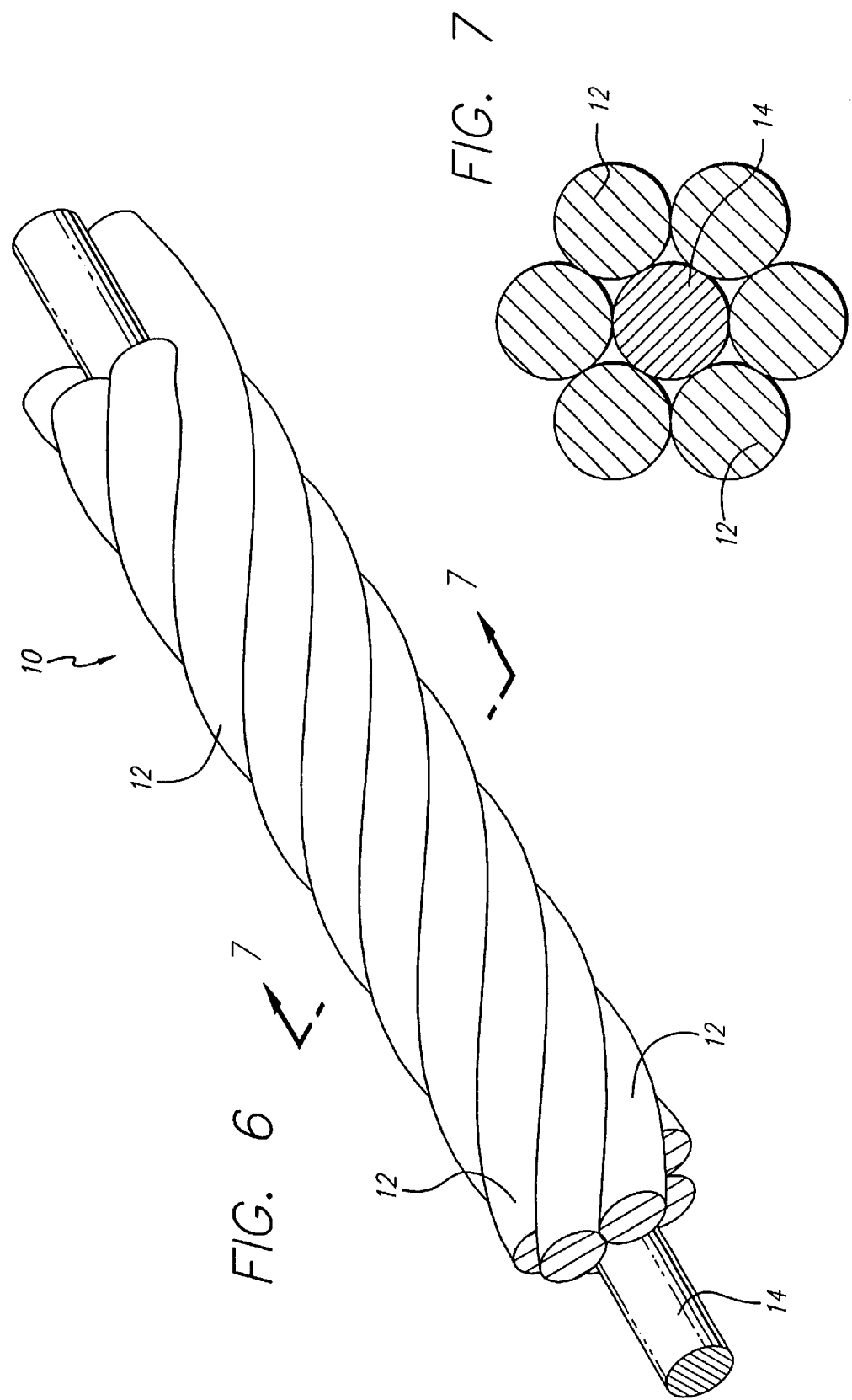

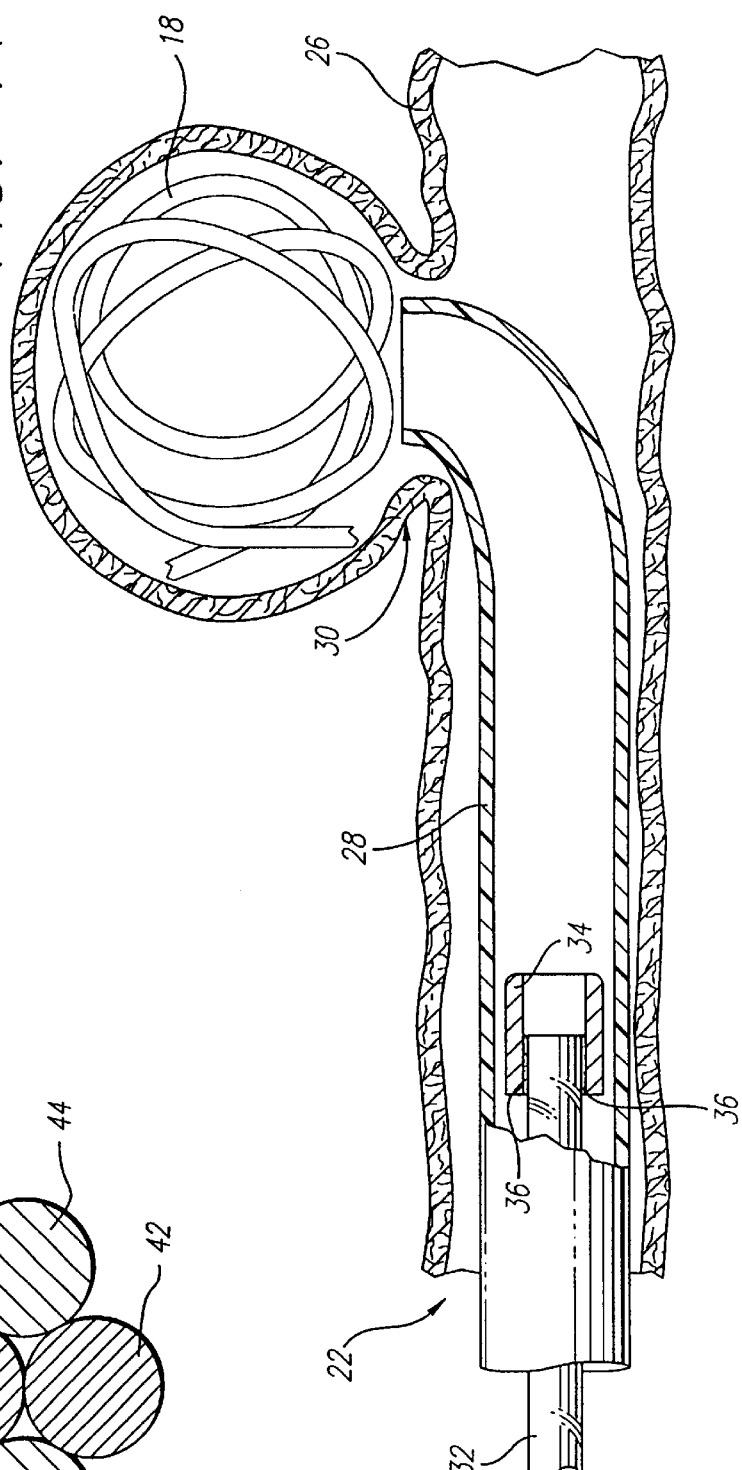
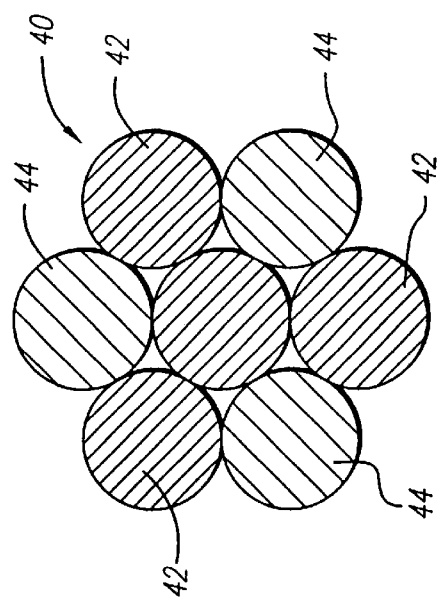

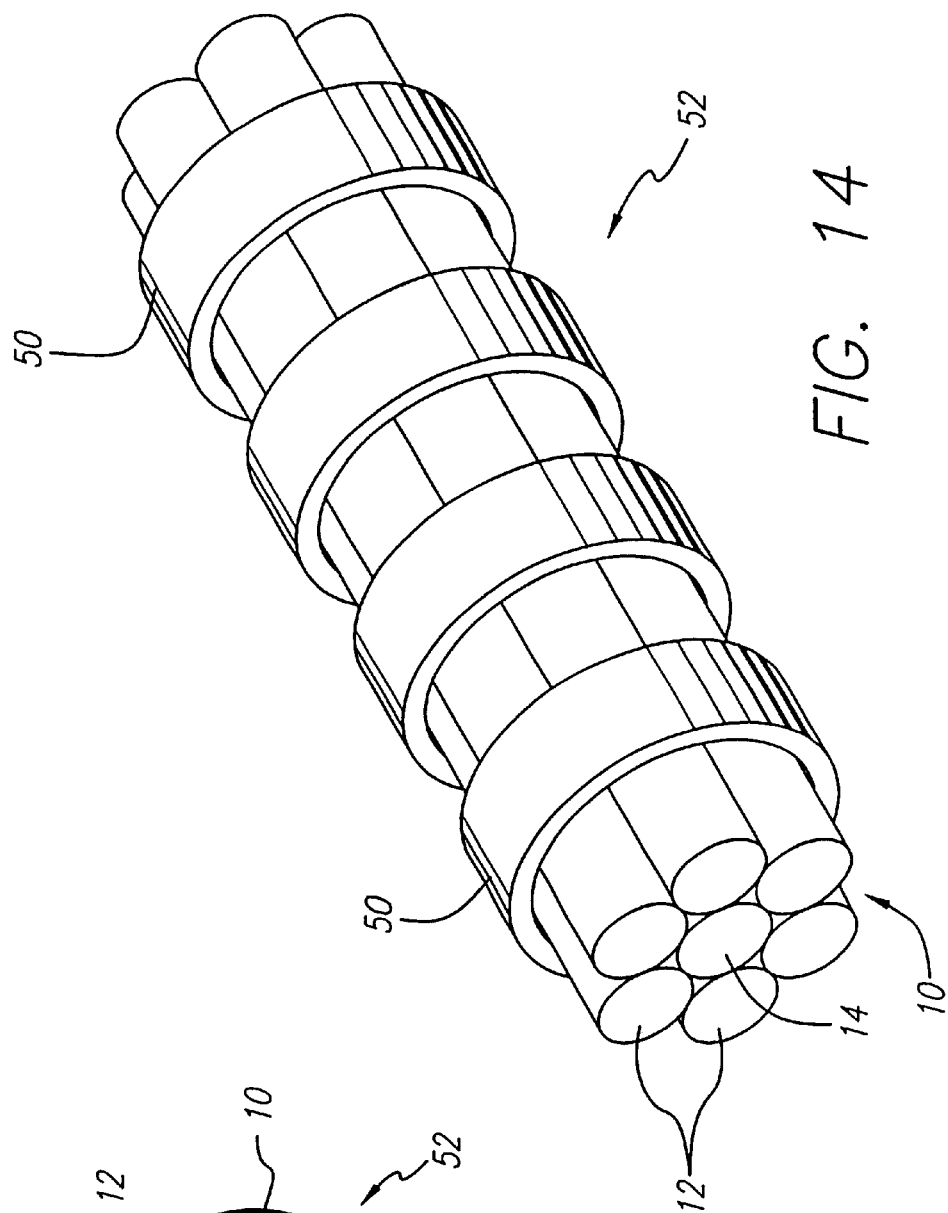

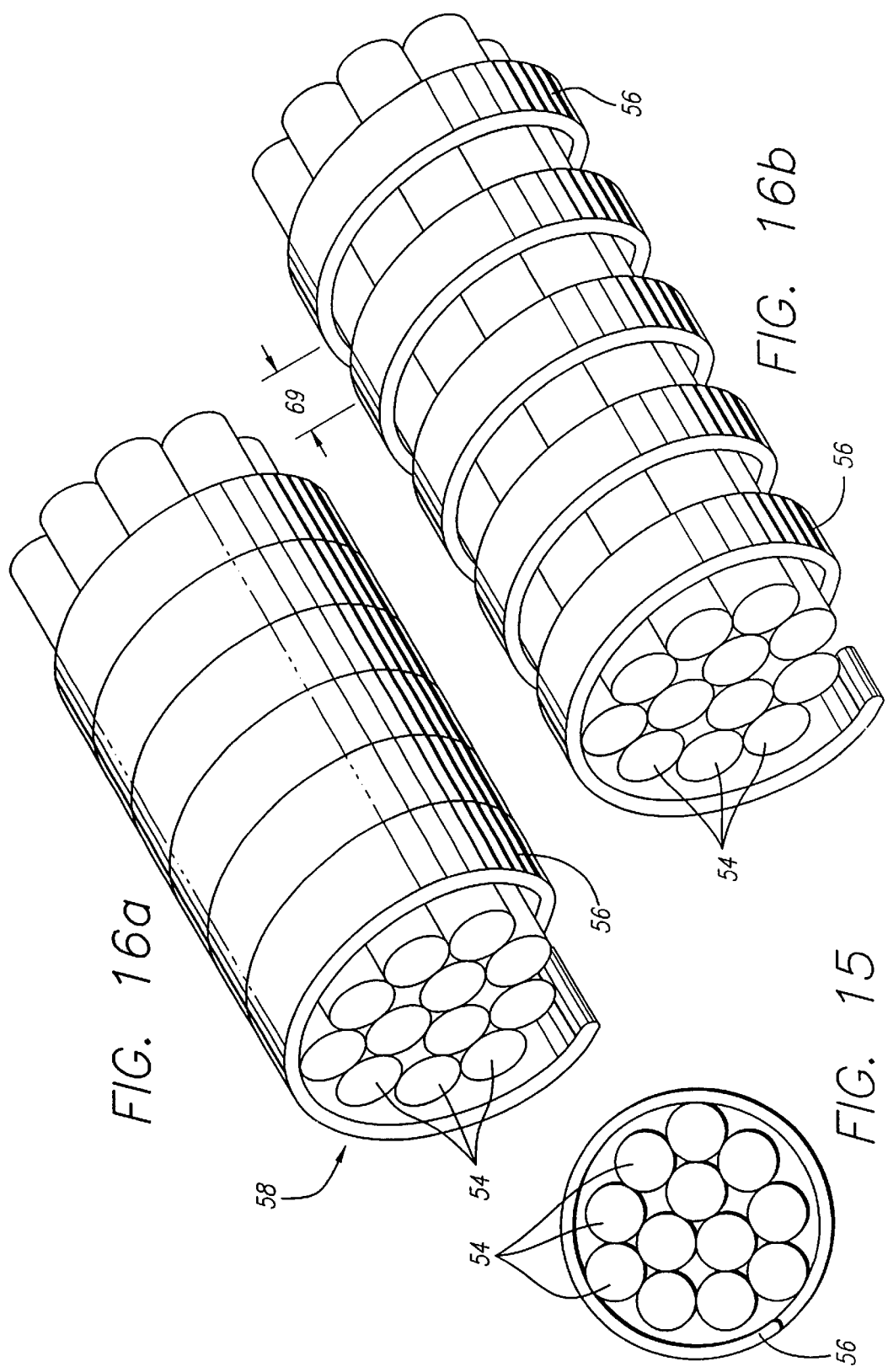

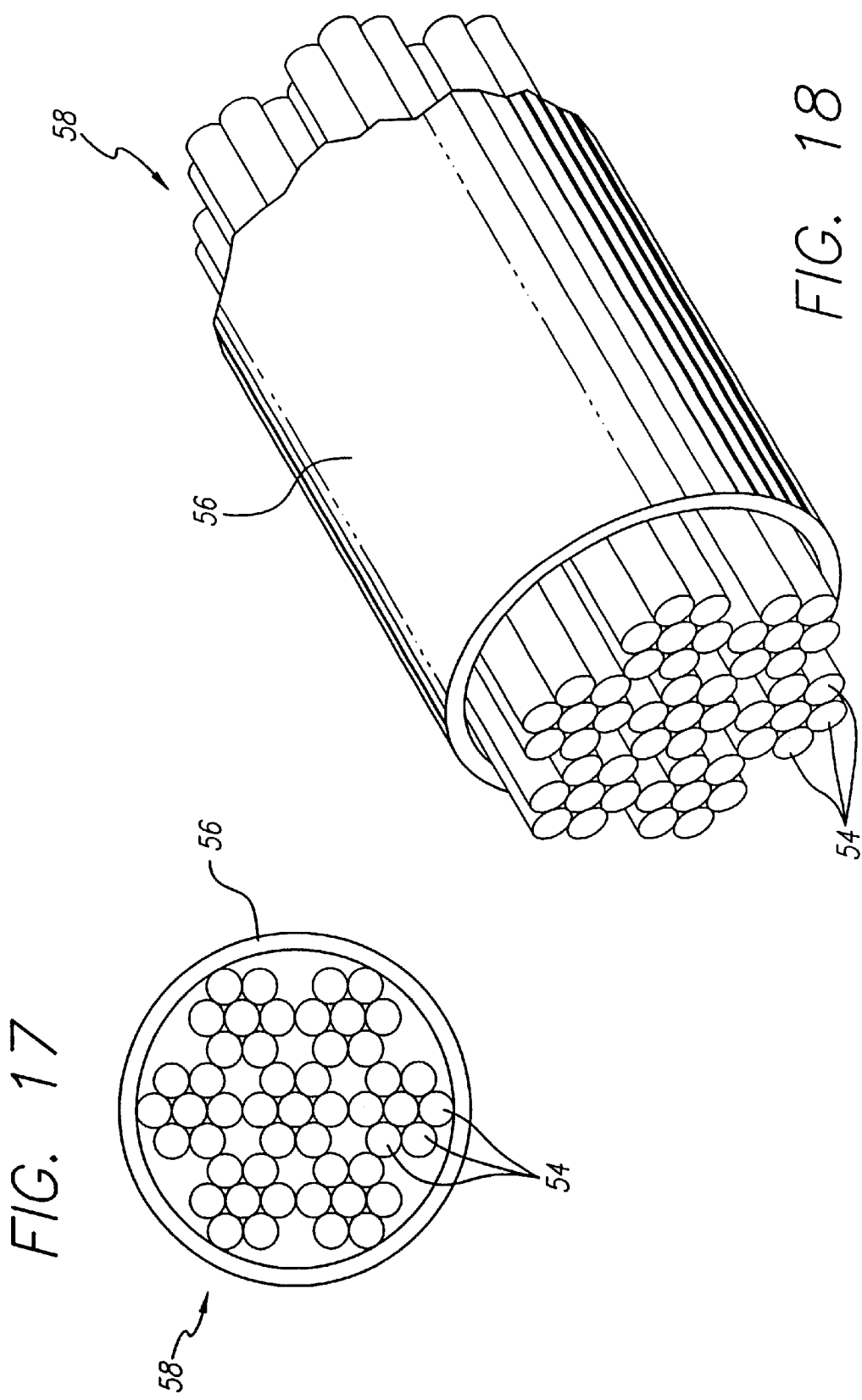

VASOOCCLUSIVE COIL

RELATED APPLICATIONS

This is a continuation of Ser. No. 09/139,258 filed Aug. 25, 1998 now U.S. Pat. No. 6,136,015.

BACKGROUND OF THE INVENTION

1. Field of the Invention

This invention relates generally to implantable devices for interventional therapeutic treatment or vascular surgery, and more particularly concerns a vasoocclusive endoluminal coil with a helical loop forming a J-shape at one or both ends of coil, and optionally with one or more loops between each end.

2. Description of Related Art

The art and science of interventional therapy and surgery has continually progressed towards treatment of internal defects and diseases by use of ever smaller incisions or access through the vasculature or body openings in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645,558, which is specifically incorporated by reference herein. That vasoocclusive device comprises one or more vasoocclusive members wound to form a generally spherical or ovoid shape in a relaxed state. The vasoocclusive members can be a helically wound coil or a co-woven braid formed of a biocompatible material, and the device is sized and shaped to fit within a vascular cavity or vesicle, such as for treatment of an aneurysm or fistula. The vasoocclusive member can be first helically wound or braided in a generally linear fashion, and is then wound around an appropriately shaped mandrel or form, and heat treated to retain the shape after removal from the heating form. Radiopacity can be provided in the vasoocclusive members by weaving in synthetic or natural fibers filled with powdered radiopaque material, such as powdered tantalum, powdered tungsten, powdered bismuth oxide or powdered barium sulfate, which can potentially be released during vascular surgery.

The delivery of such vasoocclusive devices in the treatment of aneurysms or other types of arteriovenous malformations can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

One known endoluminal coil delivery system has a mechanical release mechanism for delivering a coil that has a primary coil and a bent secondary shape in the form of additional coils. The primary coil comprises a wound resilient alloy wire such as stainless steel, platinum, or shaped memory alloy formed as a straight coil, on which a bent secondary shape with coiled ends is imposed.

Other known endoluminal coils include embolic coils with offset helical and twisted shapes having multiple axially offset longitudinal or focal axes with a secondary shape with coiled ends and a middle loop. A stretch-resistant vasoocclusive coil is also known that is formed from a helically wound primary coil and a stretch resistant member, that can also have a secondary shape with coiled ends and a middle loop; and an embolization coil having a single closed loop.

Ultrasoft embolism devices are known in which the vasoocclusive or embolism forming device is made of a material that may be a braid, coil, or chain which forms a long, thin thread-like device having little rigidity or column strength, and which can be hydraulically delivered to a site within the vasculature using an injected drug or fluid flush through a catheter. The device can be made from a wide variety of materials, and may also have end-caps to prevent the device from catching on the interior of the catheter lumen or vessel.

Highly flexible coils with secondary shape are also known that form an occlusive implant that is sufficiently flexible that it can be folded upon itself and maintain that configuration. At least a portion of distal portion of the member is formed to have a first configuration in a first state and a second configuration in a second state. The distal portion second configuration has a flow resistance substantially greater than that of the proximal portion. When discharged into a region to be occluded, the proximal portion is forced into a mass around at least a portion of the distal portion secondary structure.

It has been found that single strands of small diameter nickel-titanium alloys, as well as other metal alloys, used to form vasoocclusive devices can be kinked if twisted and pulled as can occur during or after deployment from a catheter, especially if the doctor wishes to withdraw a partially deployed coil because it is somehow incorrect in size, shape or length to repair the damage to the vessel. Also, single wire coils are more likely to cause trauma to the area to be treated if the wire is of a sufficient diameter to provide adequate tensile strength. Furthermore, such small diameter wires of some of these materials such as nickel-titanium, stainless steel and the like, are not generally radiopaque with currently available equipment, necessitating the use of radiopaque markers attached to the device, with the resultant possible diminution of functionality and increased diameter.

From the foregoing, it can be seen that embolic coils have provided important improvements in occlusion devices for the treatment of aneurysms and various types of arteriovenous malformations, but that there remain important limitations in the technology presently available to fabricate these devices. It would therefore be desirable to provide a structural element that can be incorporated into a stent, guidewire, micro-coil or the like, that offers the advantages of a shape memory alloy such as a nickel-titanium alloy, and that incorporates radiopaque material in a stable configuration that is not subject to breaking during use of the device, so that the device can be visualized under fluoroscopy. The present invention meets these and other needs.

SUMMARY OF THE INVENTION

While embolic coils of various shapes and sizes with primary and secondary configurations have been developed, single strands of small diameter nickel-titanium alloys, as well as other metal alloys used to form vasoocclusive devices, can become kinked, are more likely to cause trauma to the area to be treated if the wire is of a sufficient diameter to provide adequate tensile strength, and are not generally radiopaque with currently available equipment, necessitating the attachment of radiopaque markers to the devices.

Briefly, and in general terms, the present invention solves these and other problems by providing for an improved, easily manufactured, low friction, vasoocclusive endoluminal filler coil adapted to be placed in the vasculature for treatment of vascular formations, such as aneurysms. The coil is provided with at least one loop at the distal end of the coil that is inserted into the vascular formation that prevents the coil from migrating into an artery, prevents the distal end of the coil from puncturing tissue, and prevents coil re-alignment. The coil is advantageously made of a multi-stranded micro-cable with shape memory or superelastic qualities that give the coil a tendency to relax to a primary shape, to enable the coil to push itself against the walls of the vascular formation, to assume a three dimensional shape in the vascular formation. The invention provides particular benefits in that the coil is able, due to the multistrand construction, to be extremely soft and resilient, thus allowing the coils to be more easily placed and substantially reducing the probability that the weakened areas of the vasculature being treated will be ruptured by the coils after they are placed.

The invention accordingly provides for an occlusive device that is adapted to be inserted into a portion of a vasculature for occluding the portion of the vasculature for use in interventional therapy and vascular surgery, comprising a vasoocclusive coil with a primary coil configuration with a loop at at least one end. In one presently preferred embodiment, the loop at the end of the coil can have a J-shaped configuration, preferably with a loop diameter of about 2 mm, and in a presently preferred aspect, the coil is provided with loops at both ends, with loop at a proximal end of the coil acting as an anchor to prevent the coil from coming free from the location being treated and escaping into the vasculature. In a presently preferred embodiment both ends of the coil have a J-shape. In another presently preferred aspect, the vasoocclusive coil includes at least one loop in an intermediate position relative to the ends of the coil.

The vasoocclusive coil is preferably formed from a multi-stranded micro-cable made of a suitable material such as stainless steel or a nickel-titanium alloy, with the cable including at least one radiopaque strand, made of platinum, tungsten or gold, in order to serve as a marker during a procedure. The multi-stranded micro-cable can be configured into a vasoocclusive coil having one or both ends configured in a J-shape, to serve as a filler coil to fill a basket-type occlusion device for occluding areas of the small diameter vasculature such as an artery or vein in the brain, for example, for treatment of aneurysms and the like.

In one presently preferred embodiment, the multi-stranded micro-cable from which the vasoocclusive device is formed comprises a plurality of flexible strands of nickel-titanium alloy, the micro-cable having at least one central axially disposed radiopaque wire, such as platinum, tungsten or gold, for example, in order to provide a radiopaque marker during vascular procedures. In this preferred embodiment, the construction of the invention places the lowest tensile strength and highest flexibility member, the radiopaque marker strand, in a position in the cable which results in minimum stress on that member; at the same time, the super elastic material is in the outer strands, which have the dominant affect on performance parameters, thus enhancing the benefits of the material. Another benefit associated with the invention compared to prior art devices is that the multiple stranded cable configuration, in addition to providing a highly flexible and resilient structure, eliminates the necessity of a safety wire, since the failure of a single strand will not cause a severing of the cable. Also, the construction prevents stretching of the cable in the event of failure of a single strand, which is a significant benefit compared to constructions which have a coil around a central safety wire.

In an alternate presently preferred embodiment, the vasoocclusive device of the invention is formed from a multi stranded cable constructed of multiple twisted strands of a suitable material such as a shape memory alloy or super elastic alloy of nickel-titanium, with one or more of the twisted strands consisting of a radiopaque material. The radiopaque strand may be one or more of the peripheral twisted strands and may also include one or more central strands of the cable. In a preferred aspect of the embodiment, the cable consists of six peripheral twisted strands and a central linear core strand, one or more of which can be of radiopaque material.

In another aspect of the invention, the cable from which the vasoocclusive coil is formed can be made of linear strands that are arranged in a bundle and fastened or bound at intervals, or continuously, in order to maintain contact among the strands as the cable is bent. One or more of the strands may be radiopaque. This construction is adaptable to guidewires and other structures that must be pushable and/or torqueable, but still remain highly flexible and include radiopacity. Variations on this embodiment can include an outer sheath which consists of a solid or helically wound cover to provide enhanced torqueability and pushability. More specifically, the outer sheath can vary in thickness, stiffness of material or spring of the sheath members to provide desired variations in bending or stiffness of the cable. Such a construction is particularly adaptable to guidewires and the like, and can be varied in terms of the binding or outer layer to alter the torqueability of the cable, and the flexibility of the cable can be varied along its length by the number and sizes of the stranded members in the cable.

The occlusive device of the invention is configured to have a primary coil configuration, and a secondary, collapsed coil configuration or shape. The flexible strands in a multi-stranded micro-cable of the occlusive device can be helically wound, or can be configured as parallel, longitudinal strands. In a currently preferred embodiment, at least one of the strands comprises a super-elastic material. In another currently preferred embodiment, a plurality of the strands comprises a super-elastic material. One presently preferred super-elastic material comprises a nickel titanium alloy, that can be heat treated such that the alloy is highly flexible at a temperature appropriate for introduction into the body via a catheter, and after placement, the device will take on a shape designed to optimize the therapeutic purposes desired for the device. In another aspect of the invention, at least one of the strands comprises a shape memory material. In another currently preferred embodiment, a plurality of the strands are comprised of a shape memory material. One presently preferred shape memory material comprises a shape memory polymer. In one configuration, the strands of the micro-cable are arranged as exterior strands surrounding at least one interior strand, or core, and at least one radiopaque strand is disposed in the micro-cable, either centrally, axially disposed in the bundle of strands, or in the exterior strands surrounding the central core. The micro-cable can include a plurality of radiopaque strands, such as platinum, gold, or tungsten.

In another aspect of the invention, the strands of the micro-cable from which the occlusive device is formed can also be bundled by at least one outer cover or sheath to constrain the strands of the micro-cable about a longitudinal axis to produce a composite banded cable. The outer sheath can comprise a containment strand wound about the strands and made of a low friction material, such as a fluoropolymer, for example, or a heat shrinkable plastic tube. A plurality of heat shrink plastic covers can be placed over the strands of the micro-cable to provide bending stiffness in the cable, and the strands of the micro-cable can be banded at intervals by a plurality of bands. In another variation, a plurality of micro-cables that are arranged as parallel, longitudinal micro-cables or as helically wound micro-cables to form a composite cable can have an exterior wrapped cover that can be wound at greater or lesser intervals along the outside to provide variations in the torqueability and stiffness of the composite cable. Also, the thickness and width of the wrapping cover, as well as its material composition along the composite cable can vary in cross section along the length of the composite cable to provide bending stiffness of said cable which varies with the position on said cable. Also, the number of strands and the degree to which they extend along the composite cable can be varied within the sheath, and the outer sheath itself can be multi-layered with different materials in order to provide a graduated bending and stiffness characteristic over the length of the cable. The occlusive device thus can be formed of a plurality of micro-cables in order to provide desired bending and strength characteristics, either as helically wound micro-cables, or parallel longitudinal micro-cables having a collapsed composite cable configuration and an expanded composite cable configuration with a primary coil shape.

These and other aspects and advantages of the invention will become apparent from the following detailed description and the accompanying drawings, which illustrate by way of example the features of the invention.

BRIEF DESCRIPTION OF THE DRAWINGS

FIG. 6 is a perspective view of a radiopaque microstrand cable that can be used to form the vasoocclusive coil according to the invention.

FIG. 7 is a cross-section at 7—7 of FIG. 6.

FIG. 11 is an illustration of a J—J type vasoocclusive coil according to the invention deployed within an aneurysm.

FIG. 12 is a cross-section of an alternate micro-cable including a plurality of radiopaque strands within the cable that can be used to form the vasoocclusive coil according to the invention.

FIG. 13 is a cross-section of an alternate micro-cable that can be used to form the vasoocclusive coil according to the invention, wherein strands of the cable are arranged within an exterior binding consisting of multiple straps about the cable.

FIG. 14 is a perspective view of the micro-cable of FIG. 13.

FIG. 15 is a cross-section of an alternate micro-cable that can be used to form the vasoocclusive coil according to the invention, wherein the external binding of the cable represents a sheath wound about the cable.

FIGS. 16a and 16b are perspective view of alternative embodiments of the micro-cable depicted in FIG. 15.

FIG. 17 is a cross-section of an alternative micro-cable that can be used to form the vasoocclusive coil according to the invention, wherein a plurality of multi-strand cables are included within an external sheath surrounding the cable.

FIG. 18 is a perspective view of the embodiment of FIG. 17.

DETAILED DESCRIPTION OF THE PREFERRED EMBODIMENTS

While nickel-titanium alloys are useful in forming super-elastic or shape memory interventional devices, micro-coils formed of very small diameter wires of nickel-titanium alloy material for treatment of areas of the small diameter vasculature such as an artery or vein in the brain, for treatment of aneurysms and the like, for example, can have relatively low yield strengths and are somewhat subject to kinking, even if made of super-elastic alloy. This can create problems if the coil is to be withdrawn after being emplaced by the doctor, as for instance, if the device is too small to effectively fill the cavity to be treated. Furthermore, even solid wires of a size suitable for use in interventional devices are not very radiopaque.

Figure 1:
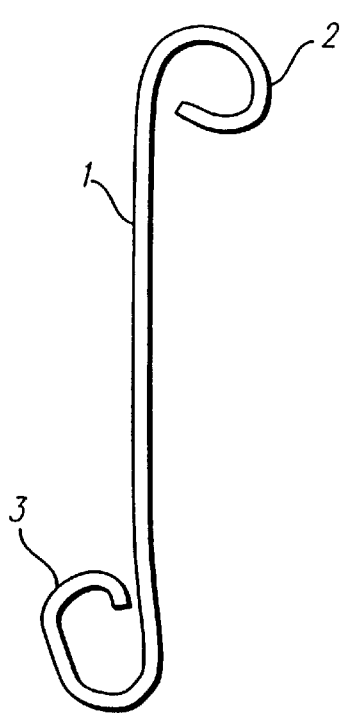
FIG. 1 is a side elevational view of a first preferred embodiment of the vasoocclusive coil according to the principles of the invention.

As is illustrated in the drawings, which are provided for the purposes of illustration and not by way of limitation, the invention is embodied in an occlusive device formed from a multi-stranded micro-cable having a plurality of flexible strands of a resilient material with the cable including at least one radiopaque strand. In a first presently preferred embodiment of the invention illustrated in FIG. 1, the occlusive device is a vasoocclusive coil 1 that is adapted to be inserted into a portion of a vasculature for occluding the portion of the vasculature for use in interventional therapy and vascular surgery. In this embodiment, the vasoocclusive coil has a primary coil configuration with a helical loop at the distal end 2 that is directed toward the location of the vasculature to be treated, and a proximal end 3 also terminating in a helical loop. The helical loop at the distal end is preferably made to have a diameter of about 2 mm in the primary coil configuration, so that the radius of the distal helical loop aids deployment within the location being treated, and acts as an anchor to help prevent coil migration into the vasculature. In a presently preferred aspect of the invention, the helical loops at the ends of the vasoocclusive coil can have a J-shaped configuration, and preferably have a loop diameter of about 2 mm. The helical loop at the proximal end of the coil further acts as an anchor to prevent the coil from coming free from the location being treated and escaping into the vasculature.

Figure 2:
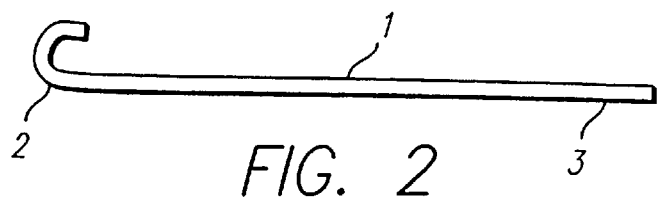
FIG. 2 is a side elevational view of a second preferred embodiment of the vasoocclusive coil according to the principles of the invention.

In another presently preferred embodiment illustrated in FIG. 2, the vasoocclusive coil 1 has a primary coil configuration with a helical loop at the distal end 2 that is directed toward the location of the vasculature to be treated, and a proximal end 3 not terminating in a helical loop. The helical loop at the distal end is preferably made to have a diameter of about 2 mm in the primary coil configuration, so that the radius of the distal helical loop aids deployment within the location being treated, and acts as an anchor to help prevent coil migration into the vasculature.

Figure 3:
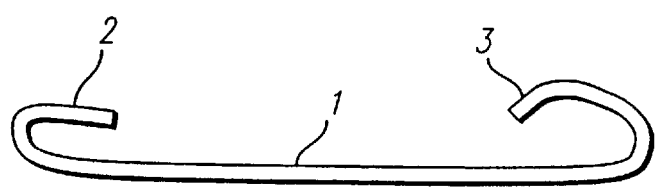
FIG. 3 is a side elevational view of a third preferred embodiment of the vasoocclusive coil according to the principles of the invention.

Another form of the double, J—J type vasoocclusive coil is illustrated in FIG. 3, in which the vasoocclusive coil has a primary coil configuration with a J-shaped helical loop at the distal end 2 that is directed toward the location of the vasculature to be treated, and a proximal end 3 also terminating in a helical loop. The helical loops at the ends of the vasoocclusive coil preferably have a loop diameter of about 2 mm.

Figure 4:
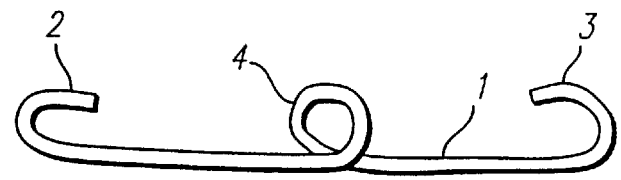
FIG. 4 is a side elevational view of a fourth preferred embodiment of the vasoocclusive coil according to the principles of the invention.
Figure 5:
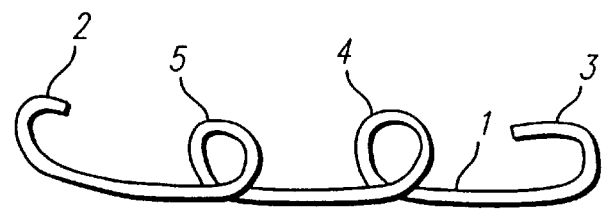
FIG. 5 is a side elevational view of a second preferred embodiment of the vasoocclusive coil according to the principles of the invention.

In another presently preferred embodiment illustrated in FIG. 4, the vasoocclusive coil 1 has a primary coil configuration with a helical J shaped loop at the distal end 2 that is directed toward the location of the vasculature to be treated, and a proximal end 3 also terminating in a helical J shaped loop. The helical loops at the two ends are preferably made to have a diameter of about 2 mm in the primary coil configuration. In another presently preferred aspect of the invention, the vasoocclusive coil can includes one or more loops 4 intermediate the ends of the coil, such as the single loop illustrated in FIG. 4, or the double intermediate loops 4, 5 as illustrated in FIG. 5.

The vasoocclusive coils of the invention are preferably formed from a multi-stranded micro-cable. In one preferred embodiment, as illustrated in FIG. 6, the vasoocclusive coils are formed from a multi-stranded micro-cable 10 that is typically approximately from 0.0021 to 0.0045 inches in diameter, and comprises a plurality of flexible strands 12 of nickel-titanium alloy, with at least one centrally, axially disposed radiopaque wire 14 which is approximately from 0.0007 to 0.0015 inches in diameter. While the above stated diameters represent those presently known to be compatible with the invention, larger or smaller diameters may be useful for particular applications. The central radiopaque wire 14 can be formed of platinum or gold, for example, or other similar suitable radiopaque metals, in order to provide a radiopaque marker of the deployed configuration of a device made of the cable during vascular surgery.

There are numerous benefits to the novel construction of the invention for use in interventional devices and the like. By using the stranded or micro-cable construction of the invention, a device made from the micro-cable becomes virtually kink resistant compared to the single strand wires now commonly used in micro-coils. The multi-strand cable construction of the invention allows the micro-wires of the cable to slip across each other and reinforce each other rather than break or take a set. Also, by incorporating a stranded radiopaque material such as platinum, tungsten or gold into the cable construction, the device is radiopaque in sizes much smaller than with other constructions. The micro-cable construction of the invention can be used to produce soft, kink resistant, radiopaque stents, guidewires, guidewire distal tips, and micro-coils.

Figure 8:
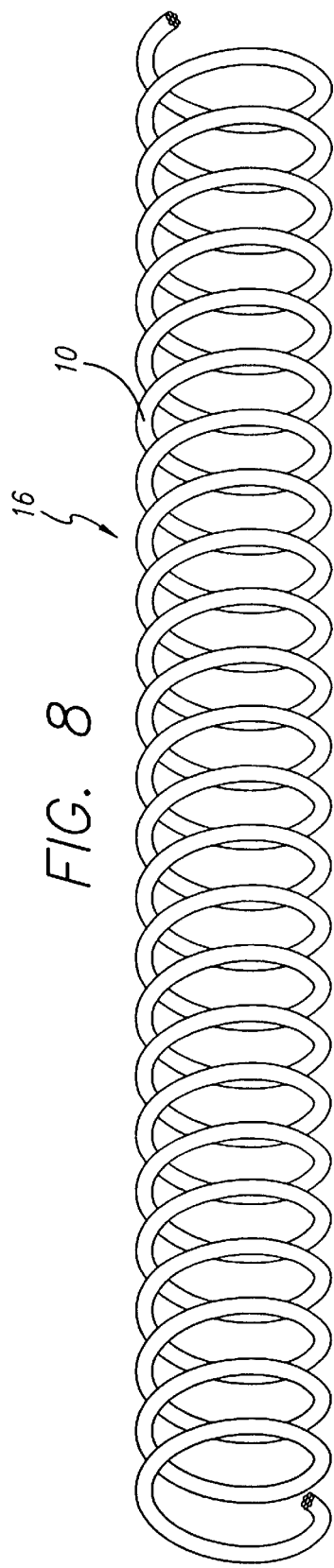
FIG. 8 is a helical vasoocclusive coil hat can be used to form the vasoocclusive coil according to the invention.

FIG. 7 is a cross-section of the micro-cable of FIG. 6 at 7—7 illustrating one presently preferred arrangement of the strands within the cable. In this embodiment, the exterior strands 12 are formed of a resilient material chosen to provide the characteristics desired for a specific application in interventional therapies. In a presently preferred embodiment, this material is a nickel titanium super-elastic alloy which is heat treated such that the alloy is highly flexible at a temperature appropriate for introduction into the body via a catheter. By choosing such a material for micro-coils and the like, the devices formed from the micro-cable can be relatively easily placed into the appropriate body cavity and after placement, the device will take on a shape designed to optimize the therapeutic purposes desired for the device. As illustrated in FIG. 7, such a cable can have a central core 14 of a radiopaque material such as gold or platinum, thus dramatically enhancing the radiopacity of the cable. Even a solid super-elastic wire of the same diameter as the cable would have substantially less radiopacity than the cable of the invention with the central gold or platinum wire and the construction of the invention provides numerous other highly desirable characteristics. Among these characteristics is the relative flexibility and resistance to kinking of the cable compared to an equivalent single wire and substantially greater accommodation of the cable to bending, etc., with resultant lessening of trauma to the surrounding tissue and ease of placement in a small body cavity. FIG. 8 illustrates a helically wound coil 16 of micro-cable 10 which is formed to fit within a micro-catheter for insertion into an area upon which a therapeutic procedure is to be performed.

Figure 9:
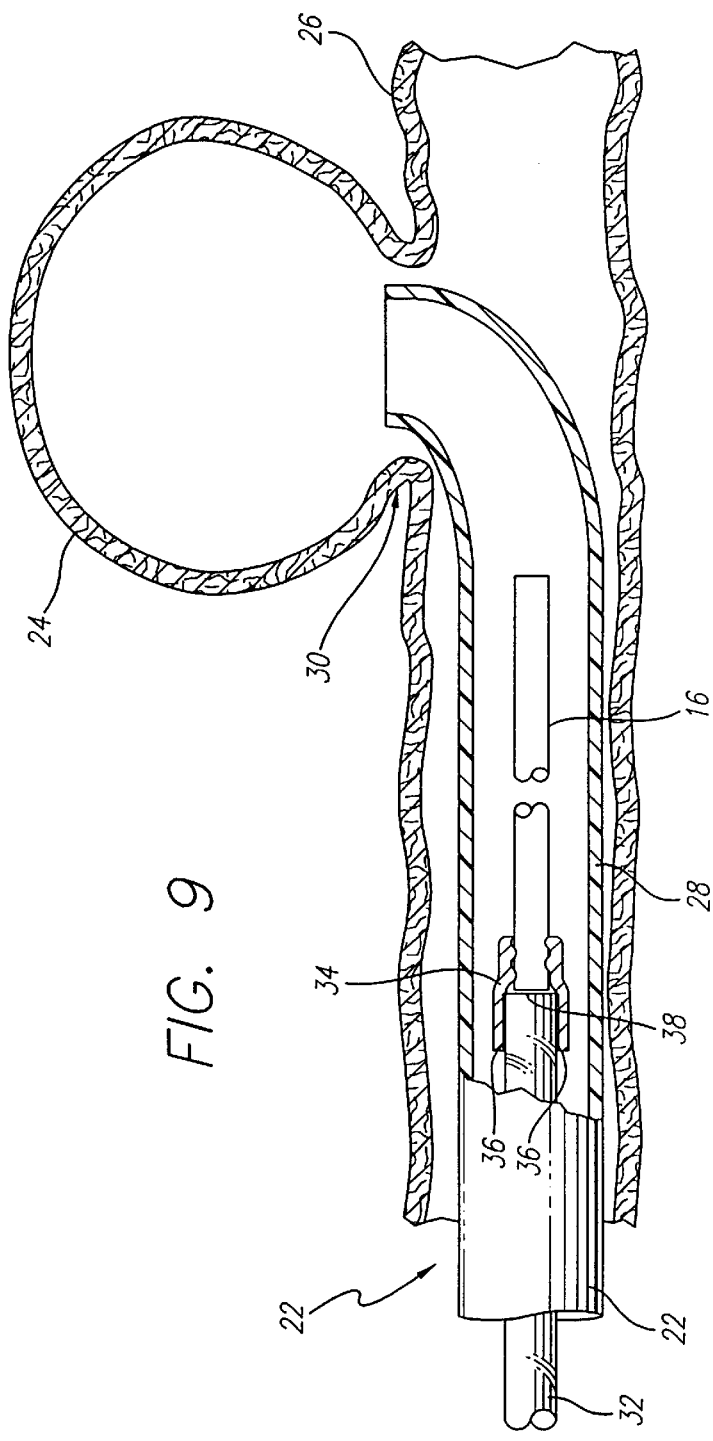
FIG. 9 is a cross section of a vascular member with an aneurysm illustrating the approach of a vasoocclusive coil in a secondary configuration towards an aneurysm.
Figure 10:
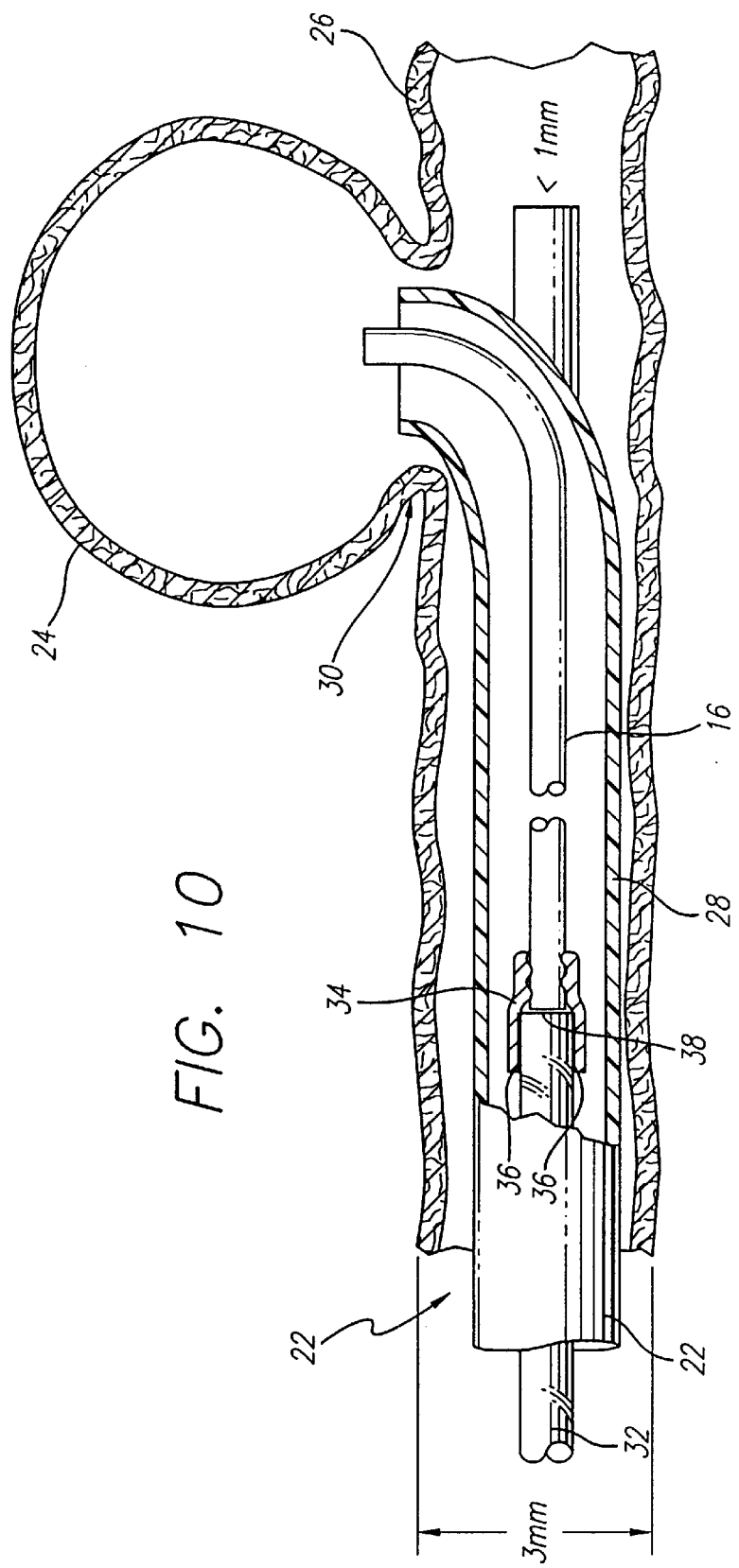
FIG. 10 is an illustration of a vasoocclusive coil being deployed within an aneurysm.

FIG. 9 is an illustration of a catheter 22 using a coil 16 as a vasoocclusive device made of the present invention and used for insertion into an aneurysm 24 projecting laterally from a blood vessel 26. The coil 16 is contained within the outer housing 28 of a micro-catheter that is used to house the coil prior to deployment. The end of the catheter housing 28 is introduced into the opening 30 of the aneurism 24 by use of a guide wire (note shown). Thereafter, the vasoocclusive coil 16, and a pusher 32 are introduced into the catheter to provide for insertion of the vasoocclusive device into the aneurysm. In a presently preferred embodiment, the coil 16 formed of the cable of the invention is retained to an optical fiber pusher 32 which is attached to the coil by a collar of shape memory plastic material 34 as described in co-pending application Ser. Nos. 09/139,258 the disclosure of which are incorporated herein by reference. As shown in FIG. 10, the coil is introduced into the aneurysm and is then pushed from the micro-catheter until it fills the cavity.

Those skilled in the art will recognize that it is sometimes the case that the vasoocclusive device must be withdrawn after it is fully or partly inserted into the aneurysm. In such a case, there is a danger that the coil will be stretched beyond its elastic range or kink, or otherwise deform and make withdrawal difficult. Those skilled in the art will also recognize that it is sometimes advantageous to form vasoocclusive devices of secondary shapes which are based upon a basic configuration of a coil or the like. The present invention includes such applications within the scope of the invention. However, when vasoocclusive devices made of even super-elastic material are used, it is sometimes the case that the devices will be stretched or kinked when withdrawal is attempted. The cable of the present invention substantially reduces the probability that kinking or stretching beyond yield will occur in a given instance, while at the same time providing radiopacity not available with other constructions. Thus, the present invention represents an important forward step in the technology of interventional therapy.

In one presently preferred embodiment, the shape memory collar 34 is heated to a temperature which allows it to be shrunk onto coil 16. The collar is attached to optical fiber pusher 32 by an adhesive 36 which retains high strength at temperatures beyond the shape memory material transition point. After insertion, and when the operator is satisfied that the device is properly deployed, light energy from a source of coherent light is introduced into the proximal end of the optical fiber (not shown) and propagated in the distal end 38 of the fiber to cause the shape memory material collar 34 to return to its previous shape and release coil 16. Those skilled in the art will recognize that the invention can also be used with a variety of other placement catheter systems, and it is not intended that the invention be limited to the placement concepts illustrated by way of example.

Those skilled in the art will recognize that a number of shaped devices may be introduced into an area to be treated depending upon its geometry and the number of devices to be inserted. FIG. 11 illustrates a J—J type coil device 18 having two J-shaped helical coil ends which has been deployed into such an aneurysm, but it will commonly be found that such one or more such coiled devices such as that shown would be used together, or would be used to supplement a different type of coiled device inserted to completely occlude flow from the artery to the aneurysm.

While one presently preferred implementation of the micro-cable of the invention has been illustrated, those skilled in the art will appreciate that other variations of the invention may have advantages for certain purposes. FIG. 12 is an example of one such construction 40 in which radiopacity is more desirable than in other forms and for that reason a number of radiopaque strands 42, in this illustration four in number, are formed into the cable along with three resilient material strands 44. It will also be appreciated that a larger or smaller number of strands may be incorporated into a given cable and the cables may be formed of multiple cables in order to provide desired bending and strength characteristics. It will also be appreciated by those skilled in the art that the invention is adaptable to the use of a variety of materials which by themselves would not have been easily adaptable to micro devices for interventional therapies. For instance, materials such as copper are useful for intrauterine devices and the like, but copper wire, even when heavily alloyed, has certain limitations for use in such devices. By use of the present invention, composite cables incorporating one or more strands of a desired material can be configured with other strands providing strength, flexibility, shape memory, super-elasticity, radiopacity or the like for previously unavailable characteristics in micro devices.

FIG. 13 illustrates a cross-section of an additional presently preferred embodiment of the invention in which the strands 12, 14 of the micro-cable 10 are bundled and banded at intervals by bands 50 to produce a composite banded cable 52 in order to provide increased flexibility without unraveling or dislocation of the strands in the cable. FIG. 14 is a perspective view of the banded cable 50 of this embodiment. While the illustrated configuration shows the strands being laid parallel within the cable, it is also possible in this construction to include both twisted cables as the primary cables 10 within the outer bands 50 to form the composite cable 52. This configuration can use one or more longitudinal strands 14 which are radiopaque, thus providing a continuous indication of radiopacity within the cable. As a further alternative embodiment, it is possible for the longitudinal cable 52 to be formed of a single inner cable 10 with bands 50.

FIG. 15 illustrates a further embodiment of the invention in which longitudinal strands of cables are contained within a wound cover 56 for the purposes of providing a composite guide wire or the like 58 having improved torqueability. Such a construction has particular advantages for guidewire designs having improved radiopacity in very small diameters. It will be appreciated that in this configuration, as well as the other longitudinally arranged multi-stranded cables, the number of strands and the degree to which they extend along the cable within the sheath is a variable which can be used to provide increased stiffness, pushability and torqueability in some sections with greater flexibility in others. Additionally, composite cables according to the invention can incorporate additional elements normally not available in solid guide wires, such as optical, thermal or ultrasound imaging elements, therapeutic agent delivery catheters, and can take advantage of materials which are not readily adaptable to prior art catheter or guide wire designs incorporating a primary wire structured element. FIGS. 16a and 16b illustrate a further variable available because of the invention; the exterior wrapped cover 56 can be wound at greater or lesser intervals 60 along the outside to provide variations in the torqueability and stiffness of the composite cable. Also, the thickness and width of the wrapping cover 56, as well as its material composition along the composite guide wire 58, can offer further capabilities for customizing the design for various applications. These advantages can be combined with the benefits of shape memory or super-elastic alloys to create guidewires and other devices with heretofore unavailable capabilities.

FIG. 17 illustrates a cross-section of a micro-cable according to the invention which has at least one overall exterior sheath to contain the micro-cable. The micro-cable may be made of one or more multiple strand elements which may further include twisted or longitudinal strands within their construction. The sheath may also be used to control the torqueability characteristics of the cable and as discussed in copending application, Ser. No. 08/986,004, the sheath may be multi-layered with different materials in order to provide a graduated bending and stiffness characteristic over the length of the cable.

It will be appreciated that a three dimensional occlusive device adapted to be inserted into a portion of a vasculature for occluding the portion of the vasculature for use in interventional therapy and vascular surgery, can be formed as described above, from at least one multi-stranded micro-cable having a plurality of flexible strands of a resilient material, with at least one radiopaque strand to provide a radiopaque marker for the device during vascular surgery. The occlusive device is configured to have a primary, coil configuration or shape such as the shapes illustrated in FIGS. 1 to 5, and a secondary elongated shape, as illustrated in FIGS. 6 and 7 for delivery through a catheter to the site to be treated. A mandrel suitable for making such shaped occlusive devices can be formed of a refractory material, such as alumina or zirconia, for example. The mandrel typically has the general three dimensional shape that the occlusive device will be given, and can have a generally helical, conical, or spherical shape, or can have a unique shape designed to provide such a primary configuration to the occlusive device. The mandrel forms a support for the winding and heat treatment of the micro-cable, plurality of micro-cables, or composite microcable occlusive device as described above, and ideally will not contaminate the occlusive device during heat treatment of the device. The surface of the mandrel preferably has a plurality of circumferential grooves for aligning the occlusive device as it is wound on the mandrel. The surface of the mandrel may also have one or more apertures for receiving one or more ends of the micro-cable, plurality of micro-cables, or composite micro-cable, to assist winding into the desired form. The wound occlusive device is then heat treated at a suitable temperature and a sufficient period of time to impart the form to the shape memory material included in the device. While heat treatment at a temperature of about 1100° F. for approximately 4 hours or more is typically sufficient to impart the form to the occlusive device when the shape memory material is a nickel titanium super-elastic alloy, but when the occlusive device includes fibers or a therapeutic agent that can be affected by heat, the temperature utilized can be substantially lowered, and the duration of heat treatment adjusted accordingly, as will be appreciated by those skilled in the art. After the heat treatment, the occlusive device is removed from the mandrel, and cold worked into the desired collapsed elongated configuration for placement into a catheter or cannula for use. When the occlusive device reaches its destination in the vasculature during vascular therapy, it assumes the primary shape imparted from the heat treatment on the mandrel.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An occlusive device for use in interventional therapy and vascular surgery adapted to be inserted into a portion of a vasculature for occluding the portion of the vasculature, comprising:
   a vasoocclusive coil having a primary coil configuration with a loop at at least one end;
   said vasoocclusive coil being formed from a micro-cable including a plurality of strands of a super-elastic material, and a radiopaque material to provide a radiopaque marker of the deployed configuration of a device made of the vasoocclusive coil during vascular surgery.

2. The occlusive device of claim 1, wherein said vasoocclusive coil has a primary coil configuration with a helical loop at a distal end of the coil.

3. The occlusive device of claim 2, wherein said helical loop has a J-shape configuration.

4. The occlusive device of claim 1, wherein said vasoocclusive coil has a primary coil configuration having two end helical loops, with a helical loop at the proximal and distal ends of the coil.

5. The occlusive device of claim 4, wherein said helical loops each have a J-shape configuration.

6. The occlusive device of claim 2, wherein said helical loop has a diameter of about 2 mm.

7. The occlusive device of claim 4, wherein said helical loops each have a diameter of about 2 mm.

8. The occlusive device of claim 1, wherein said vasoocclusive coil comprises at least one loop interediate the proximal and distal ends of the coil.

9. The occlusive device of claim 4, wherein said vasoocclusive coil comprises two loops intermediate the proximal and distal ends of the coil.

10. The occlusive device of claim 1, wherein said super-elastic material comprises a nickel titanium alloy.

11. The occlusive device of claim 1, wherein said super-elastic material comprises a shape memory material.

12. The occlusive device of claim 11, wherein said shape memory material comprises a nickel-titanium alloy.

13. The occlusive device of claim 12, wherein said shape memory nickel-titanium alloy is heat treated such that the alloy is highly flexible at a temperature appropriate for introduction into the body via a catheter, and after placement, the device will take on the primary coil configuration.

14. The occlusive device of claim 11, wherein said shape memory material comprises a shape memory polymer.

15. The occlusive device of claim 1, wherein said radiopaque material comprises platinum.

16. The occlusive device of claim 1, wherein said radiopaque material comprises tungsten.

17. The occlusive device of claim 1, wherein said radiopaque material comprises gold.

18. The occlusive device of claim 1, further comprising at least one outer sheath to provide bending stiffness for said vasoocclusive coil.

19. The occlusive device of claim 18, wherein said sheath comprises a containment strand wound about said vasoocclusive coil.

20. The occlusive device of claim 18, wherein said sheath is made of low friction material.

21. The occlusive device of claim 18, wherein said sheath is made of a fluoropolymer.

22. The occlusive device of claim 18, wherein said sheath comprises a heat shrinkable plastic tube.

23. The occlusive device of claim 18, wherein said sheath comprises a plurality of heat shrink plastic covers.

* * * * *

UNITED STATES PATENT AND TRADEMARK OFFICE
CERTIFICATE OF CORRECTION

PATENT NO.   : 6,306,153 B1
DATED        : October 23, 2001
INVENTOR(S)  : Daniel R. Kurz et al.

It is certified that error appears in the above-identified patent and that said Letters Patent is hereby corrected as shown below:

<u>Title page,</u>
Item [56], add -- FOREIGN PATENT DOCUMENTS --, and add the seventeen Foreign Patents listed on the title page of the attached patent.

Item [56], add -- OTHER PUBLICATIONS --, and add the five publications listed on title page 1 and the twelve publications listed on title page 2 of the attached patent.

Signed and Sealed this

Twentieth Day of August, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.     : 6,306,153 B1
DATED          : October 23, 2001
INVENTOR(S)    : Daniel R. Kurz et al.

It is certified that error appears in the above-identified patent and that said Letters Patent is hereby corrected as shown below:

The Certificate of Correction issued August 20, 2002 should be vacated since the Certificate of Correction was not granted.

Signed and Sealed this

Twelfth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,306,153 B1
DATED         : October 23, 2001
INVENTOR(S)   : Daniel R. Kurz et al.

It is certified that error appears in the above-identified patent and that said Letters Patent is hereby corrected as shown below:

Title page,
Item [56], References Cited, US PATENT DOCUMENTS, insert:

| | | | |
|---|---|---|---|
| 4,650,472 | | BATES | 03/17/87 |
| 5,025,799 | | WILSON | 06/25/91 |
| 5,135,494 | | ENGELSON ET AL. | 08/04/92 |
| 5,238,004 | | SAHATJIAN ET AL. | 08/24/93 |
| 5,242,462 | | EL-NOUNOU ET AL. | 09/07/93 |
| 5,379,779 | | ROWLAND ET AL. | 01/10/95 |
| 5,540,701 | | SHARKEY ET AL. | 07/30/96 |
| 5,669,931 | | KUPIECKI ET AL. | 09/23/97 |
| 5,733,329 | | WALLACE ET AL. | 03/31/98 |
| 5,749,891 | | KEN ET AL. | 05/12/98 |
| 5,766,160 | | SAMSON ET AL. | 06/16/98 |
| 5,800,453 | | GIA | 09/01/98 |
| 5,800,455 | | PALERMO ET AL. | 09/01/98 |
| 5,725,567 | | WOLFF ET AL. | 03/10/98 |

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 3,452,742 | JULY 1, 1969 | MULLER |
| 4,820,289 | APRIL 11, 1989 | COURY ET AL. |
| 4,838,803 | JUNE 13, 1989 | KONDO |
| 5,139,243 | AUGUST 18, 1992 | BALSELLS |
| 5,256,146 | OCTOBER 26, 1993 | ENSMINGER ET AL. |
| 5,304,142 | APRIL 19, 1994 | LIEBL ET AL. |
| 5,334,210 | AUGUST 2, 1994 | GIANTURCO |
| 5,527,338 | JUNE 18, 1996 | PURDY |
| 5,540,680 | JULY 30, 1996 | GUGLIELMI ET AL. |
| 5,601,600 | FEBRUARY 11, 1997 | TON |
| 5,690,667 | NOVEMBER 25, 1997 | GIA |
| 5,690,671 | NOVEMBER 25, 1997 | MCGURK ET AL. |
| 5,693,067 | DECEMBER 2, 1997 | PURDY |
| 5,718,711 | FEBRUARY 17, 1998 | BERENSTEIN ET AL. |
| 5,725,534 | MARCH 10, 1998 | RASMUSSEN |
| 5,743,905 | APRIL 28, 1998 | EDER ET AL. |
| 5,746,769 | MAY 5, 1998 | TON ET AL. |

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 3,868,956 | MARCH 4, 1975 | ALFIDI ET AL. |
| 4,494,531 | JANUARY 22, 1985 | GIANTURCO |
| 4,512,338 | APRIL 23, 1985 | BALKO ET AL. |
| 4,748,986 | JUNE 7, 1988 | MORRISON ET AL |
| 4,994,069 | FEBRUARY 19, 1991 | RITCHART ET AL. |
| 5,026,377 | JUNE 25, 1991 | BURTON ET AL. |
| 5,108,407 | APRIL 28, 1992 | GEREMIA ET AL. |
| 5,122,136 | JUNE 16, 1992 | GUGLIELMI ET AL. |
| 5,217,484 | JUNE 8, 1993 | MARKS |
| 5,228,453 | JULY 20, 1993 | SEPETKA |
| 5,250,071 | OCTOBER 5, 1993 | PALERMO |

| | | |
|---|---|---|
| 5,336,205 | AUGUST 9, 1994 | ZENZEN ET AL. |
| 5,350,397 | SEPTEMBER 27, 1994 | PALERMO ET AL. |
| 5,354,295 | OCTOBER 11, 1994 | GUGLIELMI ET AL |
| 5,312,415 | MAY 17, 1994 | PALERMO |
| 5,639,277 | JUNE 17, 1997 | MARIANT ET AL. |
| 5,649,949 | JULY 22, 1997 | WALLACE ET AL. |
| 5,222,969 | JUNE 29, 1993 | GILLIS |
| 5,607,445 | MARCH 4, 1997 | SUMMERS |
| 5,667,522 | SEPTEMBER 16, 1997 | FLOMENBLIT ET AL. |
| 5,514,176 | MAY 7, 1996 | BOSLEY, JR. |
| 5,582,619 | DECEMBER 10, 1996 | KEN |

UNITED STATES PATENT AND TRADEMARK OFFICE
CERTIFICATE OF CORRECTION

PATENT NO. : 6,306,153 B1  Page 4 of 6
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 5,562,641 | OCTOBER 8, 1996 | FLOMENBLIT ET AL. |
| 5,549,624 | AUGUST 27, 1996 | MIRIGIAN ET AL. |
| 4,994,069 | FEBRUARY 19, 1991 | RITCHART ET AL. |
| 5,226,911 | JULY 13, 1993 | CHEE ET AL. |
| 5,690,666 | NOVEMBER 25, 1997 | BERENSTEIN ET AL. |
| 5,522,836 | JUNE 4, 1996 | PALERMO |
| 5,569,245 | OCTOBER 29, 1996 | GUGLIELMI ET AL. |
| 4,768,507 | SEPTEMBER 6, 1988 | FISCHELL ET AL. |
| 4,795,458 | JANUARY 3, 1989 | REGAN |
| 4,800,882 | JANUARY 31, 1989 | GIANTURCO |
| 4,813,925 | MARCH 21, 1989 | ANDERSON, JR. ET AL. |
| 4,856,516 | AUGUST 15, 1989 | HILLSTEAD |
| 4,957,479 | SEPTEMBER 18, 1990 | ROEMER |
| 4,990,155 | FEBRUARY 5, 1991 | WILKOFF |
| 5,041,084 | AUGUST 20, 1991 | DeVRIES ET AL. |
| 5,133,732 | JULY 28, 1992 | WIKTOR |
| 5,141,502 | AUGUST 25, 1992 | MACALUSO, JR. |
| 5,147,370 | SEPTEMBER 15, 1992 | McNAMARA ET AL. |
| 5,160,341 | NOVEMBER 3, 1992 | BRENNEMAN ET AL. |
| 5,176,625 | JANUARY 5, 1993 | BRISSON |
| 5,183,085 | FEBRUARY 2, 1993 | TIMMERMANS |
| 5,690,643 | NOVEMBER 25, 1997 | WIJAY |

UNITED STATES PATENT AND TRADEMARK OFFICE
CERTIFICATE OF CORRECTION

PATENT NO.    : 6,306,153 B1
DATED         : October 23, 2001
INVENTOR(S)   : Daniel R. Kurz et al.

It is certified that error appears in the above-identified patent and that said Letters Patent is hereby corrected as shown below:

| | | |
|---|---|---|
| 5,624,461 | APRIL 29, 1997 | MARIANT |
| 5,637,113 | JUNE 10, 1997 | TARTAGLIA ET AL. |
| 5,639,277 | JUNE 17, 1997 | MARIANT ET AL. |
| 5,643,254 | JULY 1, 1997 | SCHELDRUP ET AL. |
| 5,676,697 | OCTOBER 14, 1997 | McDONALD |
| 5,234,456 | AUGUST 10, 1993 | SILVESTRINI |
| 5,304,194 | APRIL 19, 1994 | CHEE ET AL. |
| 5,342,387 | AUGUST 30, 1994 | SUMMERS |
| 5,382,259 | JANUARY 17, 1995 | PHELPS ET AL. |
| 5,441,516 | AUGUST 15, 1995 | WANG ET AL. |
| 5,443,478 | AUGUST 22, 1995 | PURDY |
| 1,341,052 | MAY 25, 1920 | F. G. GALE |
| 1,667,730 | MAY 1, 1928 | J. BIRCHARD GREEN |
| 2,078,182 | APRIL 20, 1937 | A.B. MacFARLAND |
| 2,549,335 | APRIL 17, 1951 | M. RAHTHUS |
| 3,649,224 | MARCH 14, 1972 | ANDERSON ET AL. |
| 3,334,629 | AUGUST 8, 1967 | B.D. COHN |
| 4,655,771 | APRIL 7, 1987 | WALLSTEN |
| 4,718,907 | JANUARY 12, 1988 | KARWOSKI ET AL. |
| 4,830,003 | MAY 16, 1989 | WOLFF ET AL. |
| 5,071,407 | DECEMBER 10, 1991 | TERMIN ET AL. |
| 4,638,803 | JANUARY 27, 1987 | RAND |

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 4,820,298 | APRIL 11, 1989 | LEVEEN ET AL. |
| 4,850,960 | JULY 25, 1989 | GRAYZEL |
| 4,954,126 | SEPTEMBER 4, 1990 | WALLSTEN |
| 4,957,501 | SEPTEMBER 18, 1990 | LAHILLE ET AL |
| 5,064,435 | NOVEMBER 12, 1991 | PORTER |
| 5,104,404 | APRIL 14, 1992 | WOLFF |
| 5,133,731 | JULY 28, 1992 | BUTLER ET AL. |
| 5,147,370 | SEPTEMBER 15, 1992 | McNAMARA ET AL. |
| 5,151,105 | SEPTEMBER 29, 1992 | KWAN-GETT |
| 5,176,661 | JANUARY 5, 1993 | EVARD ET AL. |
| 5,186,992 | FEBRUARY 16, 1993 | KITE, III |
| 5,203,772 | APRIL 20, 1993 | HAMMERSLAG ET AL. |

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,306,153 B1
DATED         : October 23, 2001
INVENTOR(S)   : Daniel R. Kurz et al.

It is certified that error appears in the above-identified patent and that said Letters Patent is hereby corrected as shown below:

Title page,
Item [56], References Cited, US PATENT DOCUMENTS, insert:

| | | | |
|---|---|---|---|
| 4,650,472 | | BATES | 03/17/87 |
| 5,025,799 | | WILSON | 06/25/91 |
| 5,135,494 | | ENGELSON ET AL. | 08/04/92 |
| 5,238,004 | | SAHATJIAN ET AL. | 08/24/93 |
| 5,242,462 | | EL-NOUNOU ET AL. | 09/07/93 |
| 5,379,779 | | ROWLAND ET AL. | 01/10/95 |
| 5,540,701 | | SHARKEY ET AL. | 07/30/96 |
| 5,669,931 | | KUPIECKI ET AL. | 09/23/97 |
| 5,733,329 | | WALLACE ET AL. | 03/31/98 |
| 5,749,891 | | KEN ET AL. | 06/12/98 |
| 5,766,160 | | SAMSON ET AL. | 06/16/98 |
| 5,800,453 | | GIA | 09/01/98 |
| 5,800,455 | | PALERMO ET AL. | 09/01/98 |
| 5,725,567 | | WOLFF ET AL. | 03/10/98 |

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 3,452,742 | JULY 1, 1969 | MULLER |
| 4,820,289 | APRIL 11, 1989 | COURY ET AL. |
| 4,838,803 | JUNE 13, 1989 | KONDO |
| 5,139,243 | AUGUST 18, 1992 | BALSELLS |
| 5,256,146 | OCTOBER 26, 1993 | ENSMINGER ET AL. |
| 5,304,142 | APRIL 19, 1994 | LIEBL ET AL. |
| 5,334,210 | AUGUST 2, 1994 | GIANTURCO |
| 5,527,338 | JUNE 18, 1996 | PURDY |
| 5,540,680 | JULY 30, 1996 | GUGLIELMI ET AL. |
| 5,601,600 | FEBRUARY 11, 1997 | TON |
| 5,690,667 | NOVEMBER 25, 1997 | GIA |
| 5,690,671 | NOVEMBER 25, 1997 | MCGURK ET AL. |
| 5,693,067 | DECEMBER 2, 1997 | PURDY |
| 5,718,711 | FEBRUARY 17, 1998 | BERENSTEIN ET AL. |
| 5,725,534 | MARCH 10, 1998 | RASMUSSEN |
| 5,743,905 | APRIL 28, 1998 | EDER ET AL. |
| 5,746,769 | MAY 5, 1998 | TON ET AL. |

UNITED STATES PATENT AND TRADEMARK OFFICE
CERTIFICATE OF CORRECTION

PATENT NO. : 6,306,153 B1  Page 3 of 7
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 3,868,956 | MARCH 4, 1975 | ALFIDI ET AL. |
| 4,494,531 | JANUARY 22, 1985 | GIANTURCO |
| 4,512,338 | APRIL 23, 1985 | BALKO ET AL. |
| 4,748,986 | JUNE 7, 1988 | MORRISON ET AL |
| 4,994,069 | FEBRUARY 19, 1991 | RITCHART ET AL. |
| 5,026,377 | JUNE 25, 1991 | BURTON ET AL. |
| 5,108,407 | APRIL 28, 1992 | GEREMIA ET AL. |
| 5,122,136 | JUNE 16, 1992 | GUGLIELMI ET AL. |
| 5,217,484 | JUNE 8, 1993 | MARKS |
| 5,228,453 | JULY 20, 1993 | SEPETKA |
| 5,250,071 | OCTOBER 5, 1993 | PALERMO |
| 5,336,205 | AUGUST 9, 1994 | ZENZEN ET AL. |
| 5,350,397 | SEPTEMBER 27, 1994 | PALERMO ET AL. |
| 5,354,295 | OCTOBER 11, 1994 | GUGLIELMI ET AL |
| 5,312,415 | MAY 17, 1994 | PALERMO |
| 5,639,277 | JUNE 17, 1997 | MARIANT ET AL. |
| 5,649,949 | JULY 22, 1997 | WALLACE ET AL. |
| 5,222,969 | JUNE 29, 1993 | GILLIS |
| 5,607,445 | MARCH 4, 1997 | SUMMERS |
| 5,667,522 | SEPTEMBER 16, 1997 | FLOMENBLIT ET AL. |
| 5,514,176 | MAY 7, 1996 | BOSLEY, JR. |
| 5,582,619 | DECEMBER 10, 1996 | KEN |

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 5,562,641 | OCTOBER 8, 1996 | FLOMENBLIT ET AL. |
| 5,549,624 | AUGUST 27, 1996 | MIRIGIAN ET AL. |
| 4,994,069 | FEBRUARY 19, 1991 | RITCHART ET AL. |
| 5,226,911 | JULY 13, 1993 | CHEE ET AL. |
| 5,690,666 | NOVEMBER 25, 1997 | BERENSTEIN ET AL. |
| 5,522,836 | JUNE 4, 1996 | PALERMO |
| 5,569,245 | OCTOBER 29, 1996 | GUGLIELMI ET AL. |
| 4,768,507 | SEPTEMBER 6, 1988 | FISCHELL ET AL. |
| 4,795,458 | JANUARY 3, 1989 | REGAN |
| 4,800,882 | JANUARY 31, 1989 | GIANTURCO |
| 4,813,925 | MARCH 21, 1989 | ANDERSON, JR. ET AL. |
| 4,856,516 | AUGUST 15, 1989 | HILLSTEAD |
| 4,957,479 | SEPTEMBER 18, 1990 | ROBMER |
| 4,990,155 | FEBRUARY 5, 1991 | WILKOFF |
| 5,041,084 | AUGUST 20, 1991 | DeVRIES ET AL. |
| 5,133,732 | JULY 28, 1992 | WIKTOR |
| 5,141,502 | AUGUST 25, 1992 | MACALUSO, JR. |
| 5,147,370 | SEPTEMBER 15, 1992 | McNAMARA ET AL. |
| 5,160,341 | NOVEMBER 3, 1992 | BRENNEMAN ET AL. |
| 5,176,625 | JANUARY 5, 1993 | BRISSON |
| 5,183,085 | FEBRUARY 2, 1993 | TIMMERMANS |
| 5,690,643 | NOVEMBER 25, 1997 | WUAY |

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

Page 5 of 7

It is certified that error appears in the above-identified patent and that said Letters Patent is hereby corrected as shown below:

| | | |
|---|---|---|
| 5,624,461 | APRIL 29, 1997 | MARIANT |
| 5,637,113 | JUNE 10, 1997 | TARTAGLIA ET AL. |
| 5,639,277 | JUNE 17, 1997 | MARIANT ET AL. |
| 5,643,254 | JULY 1, 1997 | SCHELDRUP ET AL. |
| 5,676,697 | OCTOBER 14, 1997 | McDONALD |
| 5,234,456 | AUGUST 10, 1993 | SILVESTRINI |
| 5,304,194 | APRIL 19, 1994 | CHEE ET AL. |
| 5,342,387 | AUGUST 30, 1994 | SUMMERS |
| 5,382,259 | JANUARY 17, 1995 | PHELPS ET AL. |
| 5,441,516 | AUGUST 15, 1995 | WANG ET AL. |
| 5,443,478 | AUGUST 22, 1995 | PURDY |
| 1,341,052 | MAY 25, 1920 | F. G. GALE |
| 1,667,730 | MAY 1, 1928 | J. BIRCHARD GREEN |
| 2,078,182 | APRIL 20, 1937 | A.E. MacFARLAND |
| 2,549,335 | APRIL 17, 1951 | M. RAHTHUS |
| 3,649,224 | MARCH 14, 1972 | ANDERSON ET AL. |
| 3,334,629 | AUGUST 8, 1967 | B.D. COHN |
| 4,655,771 | APRIL 7, 1987 | WALLSTEN |
| 4,718,907 | JANUARY 12, 1988 | KARWOSKI ET AL. |
| 4,830,003 | MAY 16, 1989 | WOLFF ET AL. |
| 5,071,407 | DECEMBER 10, 1991 | TERMIN ET AL. |
| 4,638,803 | JANUARY 27, 1987 | RAND |

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

It is certified that error appears in the above-identified patent and that said Letters Patent is hereby corrected as shown below:

| | | |
|---|---|---|
| 4,820,298 | APRIL 11, 1989 | LEVEEN ET AL. |
| 4,850,960 | JULY 25, 1989 | GRAYZEL |
| 4,954,126 | SEPTEMBER 4, 1990 | WALLSTEN |
| 4,957,501 | SEPTEMBER 18, 1990 | LAHILLE ET AL |
| 5,064,435 | NOVEMBER 12, 1991 | PORTER |
| 5,104,404 | APRIL 14, 1992 | WOLFF |
| 5,133,731 | JULY 28, 1992 | BUTLER ET AL. |
| 5,147,370 | SEPTEMBER 15, 1992 | McNAMARA ET AL. |
| 5,151,105 | SEPTEMBER 29, 1992 | KWAN-GETT |
| 5,176,661 | JANUARY 5, 1993 | EVARD ET AL. |
| 5,186,992 | FEBRUARY 16, 1993 | KITE, III |
| 5,203,772 | APRIL 20, 1993 | HAMMERSLAG ET AL. |

FOREIGN PATENT DOCUMENTS, add:

```
0 183 372 A1   6/1986    European Pat. Off.
0 382 014 A1   8/1990    European Pat. Off.
0 747 014 A1   12/1996   European Pat. Off.
0 743 047 A1   3/1997    European Pat. Off.
0 820 726 A2   1/1998    European Pat. Off.
0 824 010 A2   2/1998    European Pat. Off.
0 826 342 A1   3/1998    European Pat. Off.
592182         7/1925    France
4102550 A1     8/1991    Germany
19704269 A1    2/1997    Germany
2 066 839      7/1981    United Kingdom
WO 94/10936    5/1994    WIPO
WO 94/16619    8/1994    WIPO
WO 98/02100    1/1998    WIPO
WO 98/09570    3/1998    WIPO
WO 99/29260    6/1999    WIPO
```

OTHER PUBLICATIONS

Christos A. Athanasoulis, M.D., "Therapeutic Applications of Angiography", The New England Journal of Medicine, May 15, 1980, pp. 1117-1125 (1 of 2).
Christos A. Athanasoulis, M.D., "Therapeutic Applications of Angiography". The New England Journal of Medicine. May 22, 1980; 1174-1179 (2 of 2).
Alex Berenstein, M.D. and Irvin I. Kricheff, M.D. "Catheter and Material Selection for Transarterial Embolization: Technical Considerations". Radiology. Sep. 1979; 631-639.

UNITED STATES PATENT AND TRADEMARK OFFICE
CERTIFICATE OF CORRECTION

PATENT NO. : 6,306,153 B1
DATED : October 23, 2001
INVENTOR(S) : Daniel R. Kurz et al.

It is certified that error appears in the above-identified patent and that said Letters Patent is hereby corrected as shown below:

O.A. Battista, et al., "Colloidal Macromolecular Phenomena. Part II. Novel Microcrystals of Polymers". Journal of Applied Polymer Science. 1967; 481-498.
Sadek K. Hilal, M.D., et al., "Therapeutic Percutaneous Embolization for Extra-Axial Vascular Lesions of the Head, Neck and Spine". Journal of Neurological Surgery. Sep. 1975; 275-287.
Stephen L. Kaufman, M.D., et al., "Transcatheter Embolization with Microfibrillar Collagen in Swine". Investigative Radiology. May-Jun. 1978; 200-204.
Ashok J. Kumar, et al., "Preoperative Embolization of Hypervascular Head and Neck Neoplasms Using Microfibrillar Collagen". Journal of Neuroradiology. 1982; 163-168.
Richard E. Latchaw, M.D., et al., "Polyvinyl Foam Embolization of Vascular and Neoplastic Lesions of the Head, Neck and Spine". Radiology. 1979; 669-679.
Stewart R. Reuter, M.D., et al., "Selective Arterial Embolization for Control of Massive Upper Gastrointestinal Bleeding". American Journal of Radiology. Sep. 1975; 119-126.
Glenn H. Roberson, et al., "Therapeutic Embolization of Juvenile Angiofibroma". American Journal of Radiology. Oct. 1979; 657-663.
Sidney Wallace, M.D., et al., "Arterial Occlusion of Pelvic Bone Tumors". Cancer. Oct. 1979; 322-325 & 661-663.
Cesare Gianturco, M.D., et al., "Mechanical Devices for Arterial Occlusion". Jul. 1975; 428-435.
Sidney Wallace, et al., "Therapeutic Vascular Occlusion Utilizing Steel Coil Technique: Clinical Applications". Am. J. Roentgenol. 1976; 381-387.
James H. Anderson, et al., "Transcatheter Intravascular Coil Occlusion of Experimental Arteriovenous Fistulas". Am. J. Roentgenol. Nov. 1977; 795-798.
James H. Anderson, et al., "'Mini' Gianturco Stainless Steel Coils for Transcatheter Vascular Occlusion". Dept. of Diagnostic Radiology at the University of Texas System Cancer Center. Aug. 1978; 301-303.
Vincent P. Chuan, M.D., et al., "A New Improved Coil for Tapered-Tip Catheter for Arterial Occlusion". May 1980; 507-509
Jeff Perkins, "Shape Memory Alloys". 1095-1096

This certificate supersedes Certificate of Correction issued April 22, 2003

Signed and Sealed this

First Day of June, 2004

JON W. DUDAS
*Acting Director of the United States Patent and Trademark Office*